United States Patent [19]
Siff et al.

[11] 4,432,468
[45] Feb. 21, 1984

[54] INTRAVENOUS DELIVERY SYSTEM

[76] Inventors: Elliott J. Siff, 15 Broadview Rd., Westport, Conn. 06880; Claude L. Emmerich, 15 Hutchinson Ave., Scarsdale, N.Y. 10583

[21] Appl. No.: 232,248

[22] Filed: Feb. 6, 1981

[51] Int. Cl.³ ............................................. G01F 11/08
[52] U.S. Cl. ................................ 222/55; 137/624.14; 222/207; 604/65
[58] Field of Search ............................ 222/55, 61, 207; 128/214 F, DIG. 12, DIG. 13; 137/624.14; 239/102; 604/65, 67

[56] References Cited

U.S. PATENT DOCUMENTS

| | | | |
|---|---|---|---|
| 2,695,766 | 11/1954 | Peltz | 137/624.14 |
| 3,163,176 | 12/1964 | Darling | 137/487.5 |
| 3,431,934 | 3/1969 | Riordan | 137/624.14 X |
| 3,477,613 | 11/1969 | Mangel | 137/624.14 X |
| 3,790,042 | 2/1974 | McCormick et al. | 222/52 |
| 3,895,741 | 7/1975 | Nugent | 128/214 F X |
| 4,018,362 | 4/1977 | Ubaud | 222/55 |
| 4,037,598 | 7/1977 | Georgi | 128/214 E |
| 4,038,982 | 8/1977 | Burke et al. | 128/214 E |
| 4,204,430 | 5/1980 | Tamm et al. | 73/864.12 |
| 4,237,881 | 12/1980 | Beigler et al. | 128/214 F |

*Primary Examiner*—F. J. Bartuska
*Attorney, Agent, or Firm*—Thomas P. Murphy

[57] ABSTRACT

An intravenous delivery system for automatically controlling rate of flow of fluid to a recipient. Desired rate of flow is compared with actual rate of flow to produce error signals which are utilized to cause actual rate of flow to equal the desired rate of flow. The present invention may be used with a conventional gravity drip type IV feed or with an ambulatory system which is independent of gravity. A new quantizer for providing fluid flow independent of gravity is also disclosed.

19 Claims, 11 Drawing Figures

INTRAVENOUS DELIVERY SYSTEM

BACKGROUND OF THE INVENTION

Intraveous delivery of medicinal and nutrient fluids to patients generally consists of gravity fed systems wherein a fluid filled bottle disposed above the patient is connected by a flexible flow tube to the patient. A flow control clamp attached to the tube functions to vary the rate of fluid flow through the tube while a transparent drip chamber disposed in the flow path of the tube gives visible indication of fluid flow rate. Hospital attendants control rate of flow by adjusting the clamp until the drop rate per unit time equals a previously predetermined standard. The standard varies from patient to patient and according to the particular nature of the fluid being fed to a patient. Such a procedure is costly, inefficient, subject to dangerous error, and a waste of the limited human resources available in hospitals and similar institutions.

In addition, such a fluid delivery system generally requires that the recipient patient remain stationary usually in a prone position. The stationary requirement derives from the inherent immobility of such a system while the prone position requirement is generally demanded by hospital attendants whose duty it is to maintain fluid flow unaffected by variations in the height of the fluid bottle above the patient. While occasionally a patient may be permitted a limited amount of ambulatory freedom by placing the system on wheels which the patient may pull around, such an arrangement is cumbersome, subject to accident and disruptive of fluid flow control.

The problem of fluid flow control has been addressed by a variety of automated systems such as electronic digital control systems wherein pulse drop rate is controlled by comparing actual drop rate to command drop rate, and controlling the flow until the actual drop rate equals the desired drop rate. However, none of these systems are in widespread use presently due to high cost, high power requirements, unreliability, and unmanageable bulk and weight.

The problem of immobility of these fluid flow delivery systems seems not to have been addressed at all. Thus, ambulatory patients in and out of the hospital who require intravenous feeding must be immobilized for long periods of time while they receive necessary intravaneous feedings.

The present invention solves both of these problems in one system.

BRIEF SUMMARY OF THE INVENTION

The present invention provides a fully ambulatory and precisely controlled intravenous delivery system.

More particularly, the present invention provides a fluid flow control system comprising a stepping motor which opens and closes a flow tube valve in discrete steps in accordance with pulses generated by a unique comparator system.

First and second gate means under control of logic means provide pulses which actuate the motor to open or close the valve.

The logic means in response to pulses from first and second pulse generating means causes a predetermined number of pulses to pass through the first and second gate means in accordance to whether flow rate through the tube is greater, less than or equal to desired flow rate.

The first pulse generating means provides pulses at a rate representative of desired flow rate while the second pulse generating means provides pulses at a rate representative of actual flow rate.

In one form of the present invention the second pulse generating means provides pulses representative of fluid drip rate by counting the number of drops through a conventional drip chamber.

In another fully ambulatory form of the present invention a fluid quantizer produces fluid flow in discrete amounts from drops up to larger units and provides a pulse for each drop or unit so produced.

The quantizer which is insensitive to the effects of gravity comprises a diaphragm closing off the end of a container. The container has an input valve and an output valve. Each valve is opened or closed by the movement of a spring-loaded pivoted disk. When the disk is in a position closing the outlet valve, fluid is pressure forced into the container causing the diaphragm to flex outward. As fluid is introduced, the diaphragm flexure elongates the spring means attached to the disk. When sufficient fluid is introduced the disk is forced to a position opening the outlet valve and closing the inlet valve. At this point the flexure of the diaphragm causes a discrete amount of fluid to be ejected from the container via the outlet valve. This process is cyclic providing measured amounts of fluid through the outlet valve in a continuous fashion. A switch or other signal means operated by diaphragm motion provides a pulse at each cycle giving a measure of the actual amount of fluid being delivered. These pulses are compared with pulses representative of the desired amount of fluid to control throttling of the tube introducing fluid into a patient.

The inlet valve of the diaphragm receives fluid via a flexible bag which is disposed in a constrained enclosure with a flexible pressurized bag which provides a pressure head to force fluid through the inlet valve.

DESCRIPTION

Figure 1:
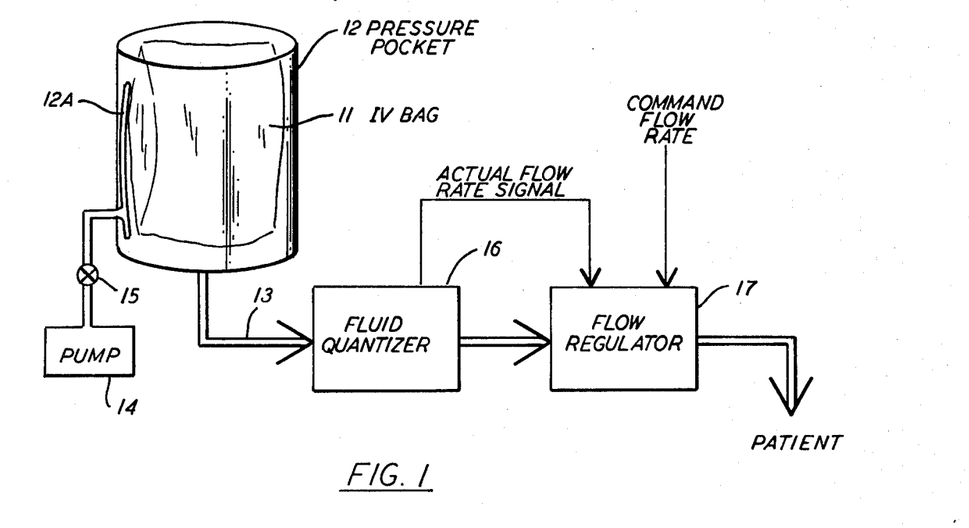
FIG. 1 illustrates in block diagram form a preferred embodiment of the present invention.

FIG. 1 is a block diagram of an apparatus 10 for controlling flow of fluid. While having general utility, the system of FIG. 1 is particularly adapted to deliver nutrient or medicinal fluids to an ambulatory recipient patient independent of gravity and without regard to the physical orientation of the patient or apparatus. To this end all its elements are comprised of light-weight, compact units including miniaturized electrical components which are capable of being worn or carried by the recipient patient in a vest or the like to enable the patient to receive the fluid at the prescribed rate while fully ambulatory.

It comprises a flexible bag 11 which contains a quantity of fluid to be delivered to a patient. The flexible bag 11 is disposed within a constrained enclosure 12 which is capable of containing an expandable balloon-type sealed compartment 12A holding gas such as air in a pressurized state. Such a condition keeps the fluid in the flexible bag under a head of pressure to force fluid from the bag 11 through a tube 13.

An air pump 14 of a source of pressurized gas is connected to compartment 12A through a one-way valve 15 and is used to pump air or gas into compartment 12A to maintain its pressurized state. The pump may be hand operable by the patient. A pressure gage (not shown) may be provided to enable the recipient patient to keep the compartment pressurized within a desired range.

The output tube 13 from flexible bag 11 is connected to a fluid quantizer 16 which converts the flow of fluid to discrete amounts of fluid occurring at a periodic rate. The amount of fluid delivered during each cycle of the quantizer may be as small as a single drop.

The output flow of fluid from the quantizer 16 is connected to flow regulator 17. The quantizer 16 also generates an electrical pulse each cycle which is provided as an input to flow regulator 17. The flow regulator 17 receives an input of electrical pulses occurring at a rate representative of the desired fluid flow rate. Since the electrical pulses from quantizer 16 are representative of actual fluid flow rate, the flow regulator 17 is constructed to compare the two pulse rates and precisely regulate flow of fluid to a patient such that the two pulse rates equalize. Thus, the flow regulator 17 continually adjusts flow of fluid delivered to a recipient patient to maintain it at the desired rate.

Figure 2:
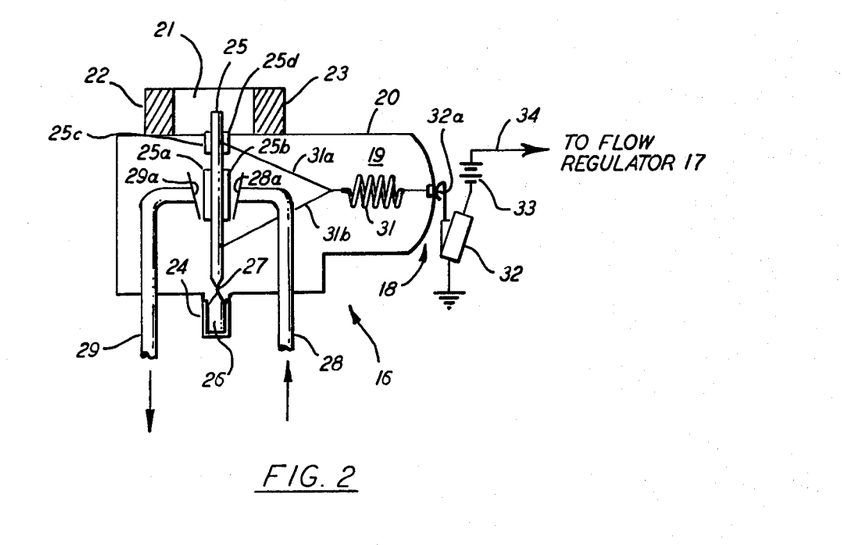
FIG. 2 is a more detailed illustration of the fluid quantizer of FIG. 1.

Referring to FIG. 2 there is shown the fluid quantizer 16 of FIG. 1. It comprises a diaphragm 18 sealing the end of volume 19 in container 20. The diaphragm 18 is made of a flexible material resistant to attack by the medicinal and nutrient fluid used and capable of expanding and contracting in accordance with the pressure of fluid within volume 19. The material may be metal such as stainless steel or plastic, rubber, or any other material having the desired properties. While the diaphragm 18 may be of any configuration, it is convenient for purposes of this invention that it be cylindrical.

The container 20 has a recess 21 formed therein. Fixedly disposed against the sides of recess 21 are permanent magnets 22 and 23.

Disposed opposite recess 21 is another recess 24 formed in container 20. A disk 25 is secured to container 20 within recess 24 by means of tab element 26 which is secured to disk 25 by means of a flexure element 27 which biases disk 25 to the left for reasons to be discussed hereinbelow. The disk 25 may be made of a magnetic metal which is resistant to the type of fluids used in the present invention.

The disk-spring assembly comprised of parts 18, 31, 31a, 31b, 25, 25a, and 25b in the quantizer must be neutrally buoyant in the fluid being administered to permit operation under all attitudes of the quantizer. Neutral buoyancy may be obtained by adding poly-styrene or other suitable closed-cell inert foam pads 25c and 25d to the disk 25. Or the disk 25 may be made hollow, if necessary, to achieve the same objective.

An inlet tube 28 communicates with volume 19 through the wall of container 20. The inlet tube has one end connected to output tube 13 from flexible bag 11. The other end 28a of tube 28 terminates within the fluid volume 19, as shown, adjacent to one side of disk 25.

An outlet tube 29 communicates with volume 19 through the wall of container 20. The outlet tube has one end connected to flow regulator 17 while its other end 29a terminates within fluid volume 19, as shown, adjacent to the other side of disk 25.

The ends 28a and 29a of tubes 28 and 29 are cut at a bias so that when disk 25 is in its extreme left position, i.e., held by magnet 22, it is flush against end 28a, thereby closing outlet tube 29. Likewise, when in its extreme right position, i.e., held by magnet 23, it is flush against end 29a, thereby closing inlet tube 28. The disk 25 may be provided with valve seats 25a and 25b which are fixedly secured to each side of the disk 25, as shown, to provide a tight seal between ends 28a and 29a when the disk is in its extreme left or right positions respectively. Valve seats 25a and 25b may be made of any suitable material, such as plastic or rubber, having adequate sealing properties.

While disk 25 is shown upright, its normal position is to the left with element 25a flush against end 29a, thus closing the outlet tube 29, by virtue of the biasing force exerted by flexure element 27.

A spring 31 is fixed at one end to diaphragm 18 and at the other end to disk 25 via struts 31a and 31b. The spring 31 is under slight tension when disk 25 is in its leftmost position closing outlet tube 29, when the diaphragm 18 is in its relaxed position.

A normally open switch 32 is positioned (by means not shown) so that its movable arm 32a just touches the end of diaphragm 18. The switch 32 is connected between ground and a battery 33 so that each time it closes a pulse is provided to flow regulator 17 via conductor 34. The switch 32 closes when diaphragm 18 expands sufficiently in the longitudinal direction. Other circuit actuating means may be used to signal each cycle of the diphragm 18. For small motions of the diaphragm 18 capacitive pick off means are more suitable as a pick off means.

As fluid enters container 20 the volume 19 enlarges forcing diaphragm 18 to expand in the axial direction. This places spring 31 under greater tension. When diaphragm 18 has elongated sufficiently the tension of spring 31 plus flexure of diaphragm 18 overcomes the holding force of magnet 22 and flexure element 27 to move disk 25 to its rightmost position, i.e., element 25b disposed against end 28A of inlet tube 28. In this position, disk 25 is under the influence of magnet 23 which exerts a holding force. The magnets 22 and 23 provide a snap action to the disk 25, assuring that disk 25 is either in one extreme position (inlet open-outlet closed) or the other extreme position (inlet closed-outlet open).

When disk 25 closes inlet tube 28, diaphragm 18 has been expanded sufficiently to close switch 32, providing a pulse on output conductor 34.

When disk 25 uncovers end 29a outlet tube 29 is opened. Fluid is forced out of outlet tube 29 due to the contraction force of diaphragm 18. As volume 19 decreases, switch 32 is opened, the tension on spring 31 reduces to the point where flexure element 27 overcomes both the spring tension and holding force of magnet 23. This forces disk 25 to its leftmost position closing outlet tube 29. Disk 25 remains in this position until enough fluid has been introduced into container 20 via now open inlet tube to overcome the holding forces of magnet 22 and flexure element 27. As should now be clear this process repeats in a cyclical fashion.

During the time that outlet tube 29 is open, fluid escapes from the diaphragm due to the contracting force thereof. The amount of fluid that escapes is a discrete amount. This discrete amount equals the change in fluid volume 19 between the extreme positions of disk 25. For purposes of description, the size of the quantizer is chosen to provide fluid amounts equal to drops although it should be noted that the present invention can be used where the amount of liquid delivered on each cycle is more than a standard drop.

Figures 3, 4:
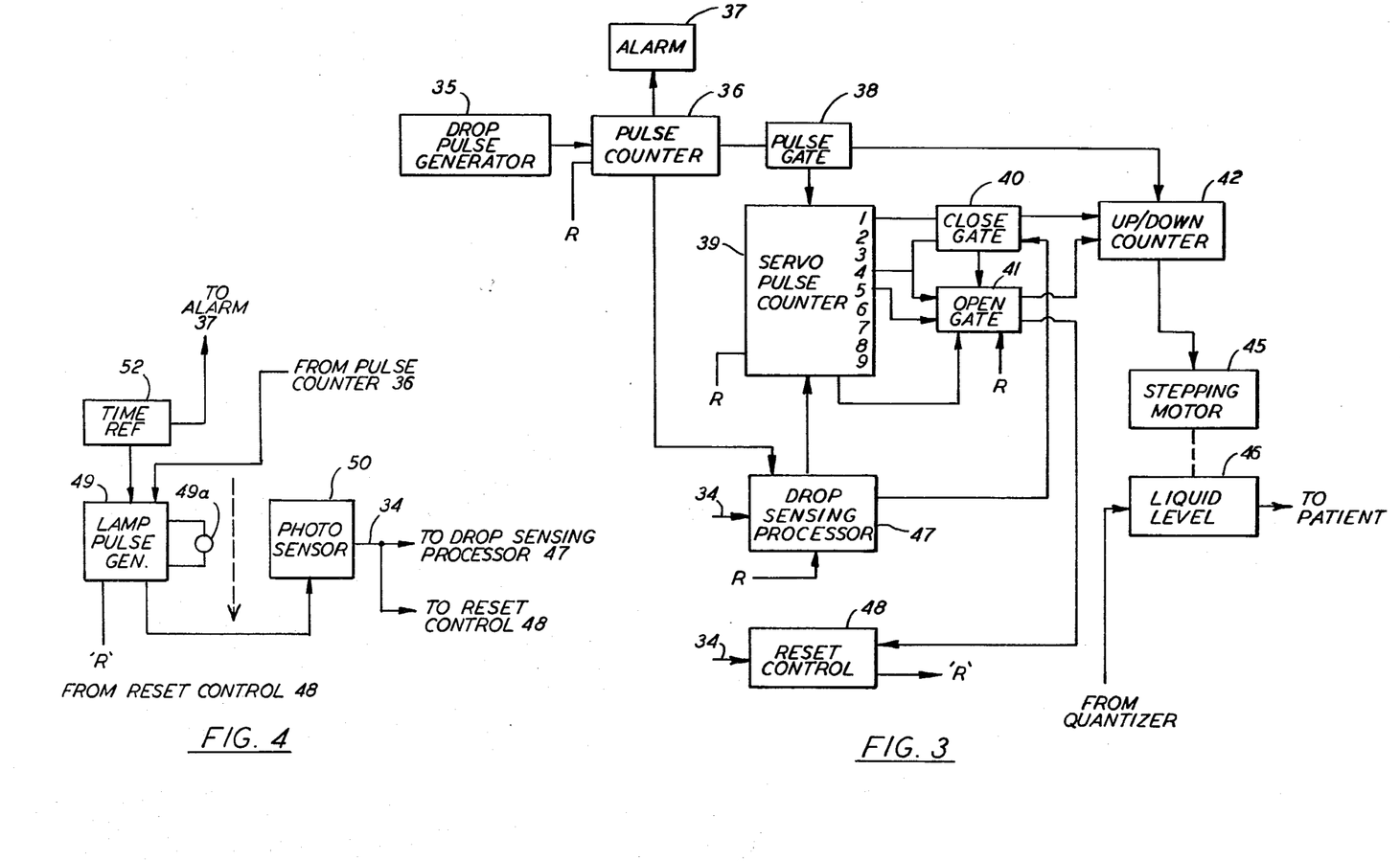
FIG. 3 is a more detailed illustration, in block diagram form, of the flow regulator of FIG. 1.
FIG. 4 is a block diagram of another embodiment of the present invention.

FIG. 3 is a more detailed block diagram view of flow regulator 17. A drop pulse generator 35 is connected to a pulse counter 36. The pulse counter provides output terminals to an alarm 37 and a pulse gate 38. A servo pulse counter 39 has an input terminal from pulse gate 38. Servo pulse counter 39 counts from 1 to 9 for each pulse provided via pulse gate 38 unless it is reset before the full count is achieved or is inhibited for other reasons. Close gate 40 receives an input from servo pulse container 39 when servo pulse counter 39 is in the "1" state or the "4" state. Open gate 41 receives an input from servo pulse counter 39 when servo pulse counter is in its "4" or "5" state.

An up-down counter 42 is connected to input terminals from close and open gates 40 and 41 as well as from pulse gate 38. The up-down counter 42 is connected to a stepping motor 45. Stepping motor 45 is connected to liquid valve 46 which it opens or closes depending on the desired drop rate. Liquid valve 46 is connected to the output tube from quantizer 16 and controls the fluid flow to the patient.

A drop sensing processor 47 is connected to receive inputs from switch 32 via connection 34, pulse counter 36 and a reset from reset control 48. It also provides output terminals to servo pulse counter 39 and close gate 40.

Reset control 48 is connected to switch 32 via connection 34, and is connected to receive an input from open gate 41. Reset control 48 provides an input to the reset terminal of pulse counter 36, servo pulse counter 39, drop sensing processor 47 and open gate 41.

For purposes of explaining the operation of the present invention with reference to FIG. 3, it is assumed that drop pulse generator 35 has been set to command twenty four drops a minute, i.e., it will generate 20 pulses between each drop if the drops are occurring at the command rate. The pulse generator 35 is a typical generator whose output frequency may be varied. In actual practice it will be seen that the output of the pulse generator is a multiple of 20 pulses.

The output from the pulse generator 35 is provided as an input to pulse counter 36. Pulse counter 36 provides an alarm signal to alarm 37 if no drop has occurred after a predetermined number of pulses, e.g., 64 pulses have been counted without the pulse counter 36 being reset by a pulse from reset control 48. As will be seen, reset control 48 provides a reset signal for each drop except in the instance where a drop occurs before servo pulse counter 39 has reached its fourth state. The alarm 37 provides an audible indication that the system is malfunctioning.

The pulse counter provides the pulses from pulse generator to pulse gate 38 which inhibits the first fifteen pulses thereof. The sixteenth and the next eight pulses step servo pulse counter 39 through its nine states unless the servo pulse counter 39 is reset earlier.

If a drop occurs after servo pulse counter 39 is reset but before it reaches its "1" state, the close gate 40 will pass three pulses from pulse gate 38 to up-down counter 42 causing it to count up by three, thus closing valve 46 three steps.

If a drop occurs before servo pulse counter reaches its "2" or "3" states, the up-down counter 42 will count up two or one counts causing valve 48 to close by two or one steps, respectively. Thus, for a drop rate too fast, the valve 46 is closed one to three steps depending on when the drop occurs.

Normally, the occurrence of a drop will activate reset control 48 to reset servo pulse counter 39. However, reset control 48 is inhibited from providing a reset pulse until it is enabled by a pulse from open gate 41. This pulse occurs when servo pulse counter 39 reaches its "4" state.

Thus, when actual drop rate of the fluid is too fast, the valve 46 will be closed by up to three steps to correct the rate. It is possible that correction for a too-fast rate will take place during several cycles, i.e., after servo pulse counter 39 is reset several times until a final correction is made, i.e., actual drop rate equals command drop rate.

When the actual drop rate is equal to the command drop rate, i.e., the drop occurs after the "3" state but before the "5" state of the servo pulsecounter 39, no correction takes place since entry into the "4" state will then cause the servo pulse counter 39 to be reset since reset control 48 is then armed to issue a reset pulse. Thus, after entering state "4" the system is always ready to be reset by the next drop.

If after the "4" state no drop occurs, entry of servo pulse counter 39 into the "5" state activates open gate 41 to cause up-down counter to count down by one, thus opening valve 46 by one step. If no drop occurs before the "6" and "7" states, the up-down counter 41 counts down by two, thus causing valve 46 to open by two more steps. Thus, when the drop rate is too slow, the valve 46 is closed by up to three steps. This correction can take place following each reset until actual drop rate equals command drop rate. If the servo pulse counter 39 reaches state "8", it is prevented from counting further by an inhibit pulse until reset. If a drop doesn't occur for a predetermined time, e.g., 64 pulses, alarm 37 signals malfunction. In addition, if drop sensing processor 47 indicates that a drop did occur before servo pulse counter 39 enters the "4" state, the servo pulse counter 39 is prevented from counting further until reset.

While the invention so far described relates to the combination described in FIG. 1, i.e., where the drops are produced by the quantizer 16 previously described, it also can function with the more conventional gravity fed drop system. In this version shown in FIG. 4, drops falling in a drip chamber are sensed by disposing a lamp pulse generator 49 and photo sensor 50 on each side of the drip chamber so that for each drop sensed, a pulse is provided on line 34 which provides the inputs to drop sensing processor 47 and reset control 48. In order to conserve energy the light emitting diode 49a is pulsed, e.g., by thirty pulses per second with each pulse lasting only one hundred microseconds each. Furthermore, the lamp pulse generator 49 is only enabled after the fifteenth pulse has occurred. Thus, lamp pulse generator 49 is connected to pulse counter 36 and is enabled on the sixteenth pulse as is the servo pulse counter 39.

The timing reference 52 is a CD4060 counter which provides the energizing pulses to lamp 49a at the desired rate and width. The timing reference 52 may also be used to supply the energizing inputs to alarm 39 which activates the alarm when a drop has occurred after pulse counter 36 has counted a predetermined number of pulses from pulse generator 35. Alternately, the alarm 37 may be caused to respond when counter 36 has reached a predetermined count.

While for purposes of explanation the pulse rate from pulse rate generator 35 was chosen so that the time interval between drops falling at the desired rate corresponds to 20 pulses, it should be noted that the actual number of pulses between drops is 16 times 20 or 320 pulses. This rate is necessary to accomplish all the functions of the system as will be seen as this description proceeds. However, to get back to the original timing, all one needs to do is divide by 16.

The drop pulse generator 35 is a free running pulse generator whose frequency is variable. To command 24 drops per minute of fluid flow, it must be set for 7680 pulses per minute which means there is an interval of 320 pulses between each drop. Other drop rates may be chosen which determines the pulse rate at which the drop pulse generator 35 must be set.

Figure 5:
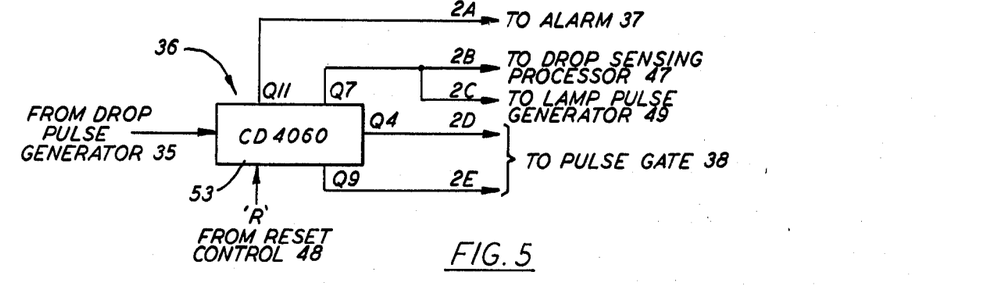
FIG. 5 illustrates pulse counter 36 in more detail.

The output of drop pulse generator 35 is fed to pulse counter 36 which is a binary counter 53. As shown in FIG. 5 the binary counter 53 provides an output Q4 and Q9 to the pulse gate 38. These outputs go high every eighth and two hundred fifty-sixth pulse, respectively.

Figure 6:
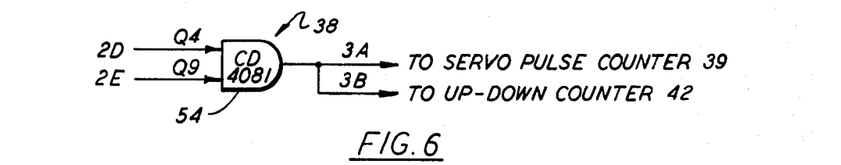
FIG. 6 illustrates the pulse gate 38 in more detail.

As seen in FIG. 6 pulse gate 38 which is an AND gate 54 provides a pulse output for each Q4 pulse while Q9 is high, i.e., from the 256th to the 512th pulse of drop pulse generator 35. Thus, the pulse gate 38 provides an output only after the fifteenth pulse.

Binary counter 53 which as can be seen is reset at the beginning of each new drop interval provides a high on Q7 at the 64th pulse from drop pulse generator 35. This signal which remains high for 128 pulses is provided as an input to drop sensing processor 47 and in one embodiment of the present invention to lamp pulse generator 49. The Q11 output from binary counter 53 is fed to alarm 37. Q11 occurs on the 1024th pulse of drop pulse generator 35, which is 3.2 times the commanded interval of 320 pulses between drops. This occurs only if pulse counter 36 has not been reset and will cause the alarm to make an audible signal.

Figure 7:
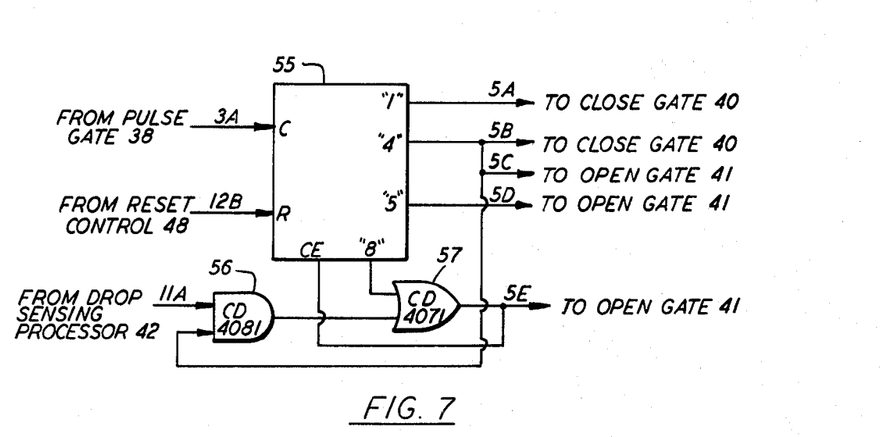
FIG. 7 illustrates the servo pulse counter 39 in more detail.

As shown in FIG. 6, the output from pulse gate 38 is fed to servo pulse counter 39 and up-down counter 42. FIG. 7 shows that the servo pulse counter 39 is a combination of a decoded decimal counter 55, an AND gate 56, and an OR gate 57. These components and all the others in FIGS. 5–11 are commercially available as identified by their numbers in the drawings.

Every 16th pulse of the drop pulse generator 35 which appears an an output from pulse gate 38 starting at the 256th pulse of the drop pulse generator 38 advances the count of servo pulse counter by one. Open gate 41 and close gate 40 receive pulses when servo pulse counter 39 is in the "1", "4" and "5" states as indicated in FIG. 7. In addition, if the drop sensing processor 47 (shown in FIG. 10) is high when the servo pulse counter 39 goes into the "4" state, the servo pulse counter is prevented from counting further until it is reset. Likewise, as can be seen from FIG. 7, if the servo pulse counter 39 reaches state "8", it is prevented from advancing further until reset.

Figure 8:
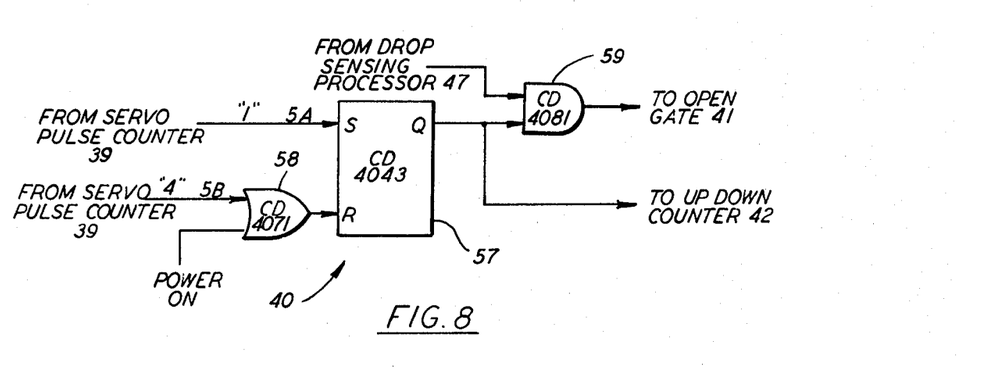
FIG. 8 illustrates the close gate 40 in more detail.

FIG. 8 shows close gate 40. It comprises a flip-flop 57, an OR gate 58 and an AND gate 59. Close gate 40 is reset when power is turned on. When the servo pulse counter 39 enters state "1", the flip-flop 57 goes high sending an UP signal to up-down counter 42 and a pulse to open gate 41 provided there is a high at and gate 59 from drop sensing processor 47. As also seen in FIG. 8, the flip-flop 57 is reset when servo pulse counter 39 enters the "4" state.

Figure 9:
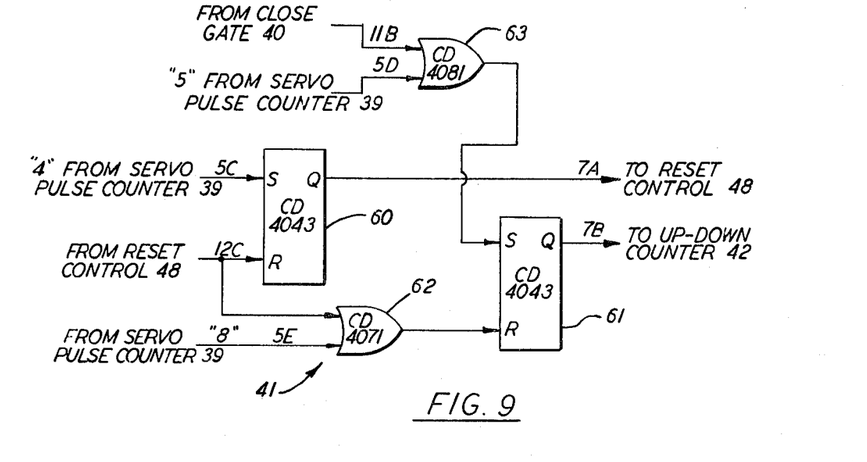
FIG. 9 illustrates the open gate 41 in more detail.

FIG. 9 shows the open gate 41. It comprises two flip-flops 60 and 61 and OR gates 62 and 63. Each flip-flop 60 and 61 is reset at the beginning of each new drop-time interval. Flip-flop 61 is also reset when servo pulse counter enters the "8" state. The output from flip-flop 60 sets reset control 48 high when servo pulse counter 39 enters the "4" state as seen from the drawing. As also seen from the drawing, up-down counter 42 is enabled either when servo pulse counter 39 enters the "5" state or the "1" state (via the close gate signal). It is prevented from counting during the "4" state or while the servo pulse counter 39 is blocked from counting.

The up-down counter 42 provides up to three down or up counts to stepping motor 45 for each cycle to close or open, respectively, the fluid valve 46 in discrete steps.

Figure 10:
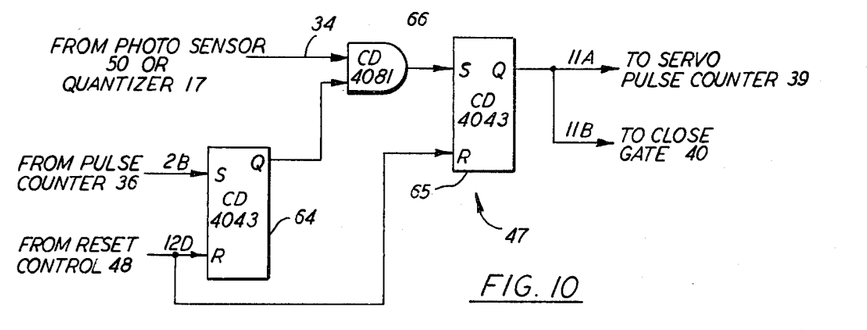
FIG. 10 illustrates the drop sensing processor 47 in more detail.

As seen in FIG. 10 drop sensing processor 47 comprises flip-flops 64 and 65 and an AND gate 66. Each of flip-flops 64 and 65 is reset at the beginning of each new drop-time interval. Flip-flop 64 remains reset until the 64th pulse from pulse counter 36. This prevents any output signals from appearing for some time after reset which prevents the system from being locked in the reset state. When after the 64th pulse, a drop is sensed either by quantizer 17 or in the embodiment of FIG. 4 by a signal from photosensor 50, flip-flop 65 is set issuing the drop signal to close gate 40 and servo pulse counter 39.

Figure 11:
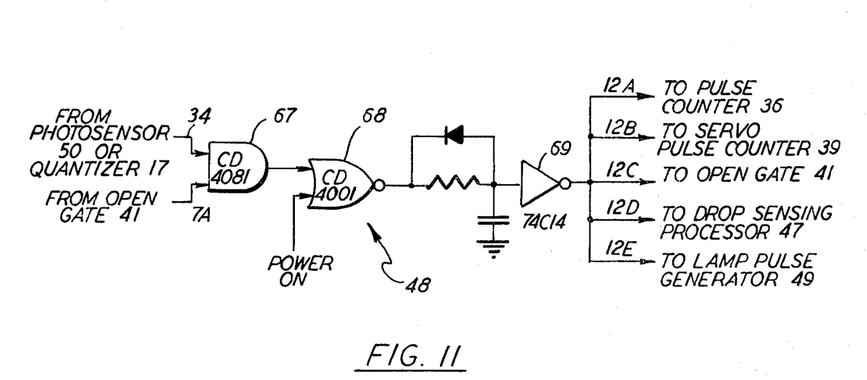
FIG. 11 illustrates the reset control 48 in more detail.

The reset control 48 is shown in FIG. 11. It comprises an AND gate 67, OR gate 68 and amplifier 69. It is reset by power on. When AND gate 67 receives a high from photo sensor 50 or quantizer 17 coincident with a signal from open gate, reset control 48 provides a reset signal to pulse counter 36, servo pulse counter 39, open gate 41, drop sensing processor and in the embodiment of FIG. 4 to lamp pulse generator 49.

In order to conserve power used by stepping motor 45 a pulse shaper and encoder are included within the up-down counter 42 or alternately between the up-down counter 42 and stepping motor 45. The pulse shaper which is of conventional structure has an output which goes high when a pulse arrives from the up-down counter 42. Within approximately 25 milliseconds, this pulse is returned to zero until it receives the next pulse. The encoder which is also of conventional construction insures that the appropriate stepping motor's winding is pulsed depending upon the two least-significant bit values from the up-down counter 42. The foregoing arrangement insures that the stepping motor is energized only for 25 milliseconds for each pulse from the up-down counter 42 and is not continuously on. This arrangement results in a substantial saving in power used by the stepping motor 45.

Other modifications of the present invention are possible in light of the above description which should not be construed as limiting the invention beyond those limitations expressly made in the claims which follow:

What is claimed is:

1. A system for controlling flow of fluid, comprising in combination;
   a flexible bag containing fluid having an output tube,
   first means comprising,
   an enclosure containing an expandable sealed compartment including,
   means for maintaining pressure within said compartment at an operable level,
   said flexible bag being disposed within said enclosure for forcing fluid through said output tube,
   second means comprising,
   a container having a diaphragm fixed thereto capable of expanding in one direction,
   inlet valve means connected to said output tube,
   outlet valve means,
   fourth means disposed within said container having a first position closing said outlet valve means and opening said inlet valve means and a second position opening said outlet valve means and closing said inlet valve means,
   spring means disposed within said container for moving said fourth means from said first position to said second position each time sufficient fluid has been introduced into said container to expand said diaphragm a predetermined amount thereby forcing a discrete amount of fluid through said outlet valve means,
   fifth means moving said fourth means back to said first position each time said discrete amount of fluid is emitted through said outlet valve,
   third means connected to said outlet valve means providing fluid flow in accordance with a predetermined amount.

2. A system according to claim 1 wherein said fourth means comprises,
   disk means disposed within said container,
   said fifth means pivotally connecting said disk means at one end to said container,
   said fifth means including a thin flexible element normally biasing said disk means to said first position.

3. A system according to claim 2 wherein said spring means includes,
   a slightly tensioned spring being placed under sufficient tension each time said diaphragm expands said predetermined amount to overcome the bias of said thin flexible element to cause said disk means to move to said second position.

4. A system according to claim 3 further including,
   circuit actuating means providing an electrical pulse each time said diaphragm expands said predetermined amount whereby the pulse rate is representative of fluid flow rate through said second means.

5. A system according to claim 4 further including,
   magnet means fixed to said container,
   at least a portion of said disk means comprising magnetic material in operative association with said magnet means whereby a snap-action is provided to said disk when said disk nears said first or second position.

6. A system according to claim 5 wherein said container has a volumetric size such that each discrete quantity emitted through said outlet valve is the equivalent of a drop of fluid.

7. A system according to claim 6 wherein said third means comprises,
   a valve included in said outlet valve means,
   servo motor means connected to said valve for closing said valve a discrete amount in response to each positive pulse received and opening said valve a discrete amount in response to each negative pulse received,
   generator means providing pulses at a rate representative of desired fluid flow rate through said outlet valve means,
   circuit means connected to said generator means and said switch means providing positive pulses to said servo motor means when actual fluid flow rate is faster than desired fluid flow rate or negative pulses to said servo motor means when actual fluid flow rate is slower than desired fluid flow rate until actual and desired fluid flow rates equalize.

8. A system according to claim 7 wherein said circuit means comprises,
   up-down counter means connected to said generator means,
   gating means connected to said up-down counter means for causing said up-down counter means to provide one or more positive pulses to said servo motor means when said actual flow rate is faster than said desired flow rate or one or more negative pulses to said servo motor means when said actual flow rate is slower than said desired flow rate.

9. A system according to claim 8 wherein said circuit means further comprises,
   servo pulse counter means connected to said generator means for counting through eight states,
   reset control means connected to said switch means for resetting said servo pulse counter means on occurrence of a pulse from said switch means after said servo pulse counter means has entered its fourth state,
   gate means providing a positive enabling pulse to said up-down counter means during the first three states of said servo pulse counter means and a negative enabling pulse to said up-down counter means during the fifth, sixth and seventh states of said servo pulse counter means whereby said up-down counter means provides up to three positive pulses to said servo motor means during said positive enabling pulse and up to three negative pulses to said up-dwon counter means during said negative pulses.

10. A system according to claim 9 further comprising,
    sixth means connected to said switch means and said gate means for limiting the duration of said positive enabling pulse to the time interval after the occurrence of a pulse from said switch means.

11. A system according to claim 10 further including power conserving means for limiting the time said servo motor means is energized by each pulse from said up-down counter means.

12. A system according to claim 1 wherein said means for maintaining pressure includes,
    a hand pump connected to said compartment for pumping gas into said compartment.

13. A quantizer for delivering fluid in discrete units, comprising in combination,
    a container,
    a source of pressurized fluid,
    diaphragm means fixed to one end of said container capable of expanding in one direction,
    inlet valve means connected to said source of pressurized fluid,
    outlet valve means, first means disposed within said container means having a first position closing said outlet valve means and opening said inlet valve means and a second position opening said outlet valve means and closing said inlet valve means, spring means disposed within said container means for moving said first means from said first position to said second position each time sufficient fluid has been introduced into said container means to expand said container means a predetermined amount thereby forcing a discrete amount of fluid through said outlet valve means, second means moving said first means back to said first position each time said discrete amount of fluid is emitted through said outlet valve means.

14. A quantizer according to claim 13 wherein said first means comprises, disk means disposed within said container means, said second means pivotally connecting said disk means at one end of said container means.

15. A quantizer according to claim 14 wherein said second means further comprises, a thin flexible element normally biasing said disk means to said first position.

16. A quantizer according to claim 14 wherein said spring means comprises, a slightly tensioned spring connected between said disk means and said container means, said spring being placed under sufficient tension each time said diaphragm means expands said predetermined amount to overcome the bias of said thin flexible element and magnet force to cause said disk means to move to said second position.

17. A quantizer according to claim 16 further including, switch means disposed adjacent to said diaphragm means providing an electrical pulse each time said diaphragm means expands said predetermined amount whereby the pulse rate is representative of fluid flow out of said outlet valve means.

18. A quantizer according to claim 17 wherein said container means has a volumetric size such that each discrete unit of fluid emitted through said outlet valve is the equivalent of a drop of fluid.

19. A quantizer according to claim 18 further including, magnet means fixed to said container, at least a portion of disk means comprising magnet material in operative association with said magnetic means whereby a snap-action is provided to said disk means when said disk means nears said first or second position.

* * * * *